(12) United States Patent
Fernandez

(10) Patent No.: US 6,485,981 B1
(45) Date of Patent: Nov. 26, 2002

(54) METHOD AND APPARATUS FOR IMAGING AND DOCUMENTING FINGERPRINTS

(75) Inventor: Salvador M. Fernandez, Hartford, CT (US)

(73) Assignee: Ciencia, Inc., East Hartford, CT (US)

( * ) Notice: Subject to any disclaimer, the term of this patent is extended or adjusted under 35 U.S.C. 154(b) by 0 days.

(21) Appl. No.: 09/362,517

(22) Filed: Jul. 28, 1999

Related U.S. Application Data
(60) Provisional application No. 60/094,505, filed on Jul. 29, 1998.

(51) Int. Cl.[7] .............................................. G01N 33/92
(52) U.S. Cl. ........................ 436/71; 436/172; 436/164
(58) Field of Search ............................... 436/71, 86, 87, 436/88, 164, 172, 89, 90, 111; 422/82.08

(56) References Cited

U.S. PATENT DOCUMENTS

| 4,898,799 A | * | 2/1990 | Fujimaki ................. 430/58.65 |
| 5,221,627 A | * | 6/1993 | Grigg et al. .................... 436/89 |
| 5,616,502 A | * | 4/1997 | Haugland et al. ............. 436/86 |
| 6,127,189 A | * | 10/2000 | Joullie et al. ................ 436/111 |
| 6,225,050 B1 | * | 5/2001 | Waggoner ....................... 436/6 |

* cited by examiner

Primary Examiner—Jill Warden
Assistant Examiner—Sam Siefke
(74) Attorney, Agent, or Firm—Alix, Yale & Ristas, LLP

(57) ABSTRACT

The invention relates to a method and apparatus for imaging and documenting fingerprints. A fluorescent dye brought in intimate proximity with the lipid residues of a latent fingerprint is caused to fluoresce on exposure to light energy. The resulting fluorescing image may be recorded photographically.

12 Claims, 2 Drawing Sheets

METHOD AND APPARATUS FOR IMAGING AND DOCUMENTING FINGERPRINTS

CROSS-REFERENCE TO RELATED APPLICATION

This application claims the priority of U.S. provisional patent application Ser. No. 60/094,505, which was filed on Jul. 29, 1998, titled METHOD AND APPARATUS FOR IMAGING AND DOCUMENTING FINGERPRINTS.

This invention was made with Government support under contract number DE-FG02-98ER82553 awarded by the Department of Energy. The Government has certain rights in this invention.

1. Field of the Invention

The invention relates to the detection and documentation of latent fingerprints. More specifically, the invention relates to a method and apparatus for chemically imaging latent fingerprints and documenting the disclosed fingerprint images using conventional or electronic photographic techniques.

2. Background of the Invention

A fingerprint is perhaps the most powerful and valuable evidence capable of linking a suspect to the crime scene. Fingerprints which are found on surfaces can be generally classified into three types: visible, impression and latent fingerprints. Of these, visible fingerprints can be analyzed and documented by photographing them directly, while impression fingerprints can usually be photographed using special lighting techniques. Latent fingerprints, however, are difficult to detect and prior to documentation and analysis must first be made visible, that is, they must be "imaged".

There are three general classes of techniques for making latent fingerprints visible: physical, chemical and instrumental techniques. This application is concerned primarily with chemical techniques for imaging and documenting fingerprints from the residues which form the latent fingerprint itself. These residues comprise a variety of substances from the body which are exuded through the skin of the fingertips or which are produced in other locations on the body and transferred to the fingers through contact with those areas.

The primary component of a fingerprint is ordinary perspiration. This mostly contains water which evaporates readily from a fingerprint and leaves a residue of various chemicals. The residue contains both inorganic and organic materials some of which can remain detectable on a surface long after the water component of the perspiration has evaporated. These chemicals include water soluble amino acids, peptides, salts, glucose, lactic acid, ammonia, riboflavin, and water insoluble oils and other sebaceous secretions (generally referred to as lipids). For the purposes of this application, the term "fingerprint" is used to describe both the chemical residue left when a person touches an object, or the image formed by the residue.

From the time the detection and use of fingerprints as a forensic tool began in the nineteenth century a variety of chemical methods have been developed which utilize the various substances contained in the residues of a latent fingerprint for creating an observable image. For example, silver nitrate was found to react with the salt in a latent print which, through exposure to an actinating light source, forms a visible fingerprint image. However, exposure to moisture can readily remove salts from a latent fingerprint making the print undetectable by this method.

In the ninhydrin technique the amino acids present in a latent fingerprint are reacted with triketohydrinden hydrate to create a visible purple-blue fingerprint image. The ninhydrin technique takes advantage of the reaction of the long-lasting and environmentally durable amino acids which may be present in a fingerprint. However, it is well known that not all fingerprints contain amino acids and consequently, this technique will not disclose all latent prints which may be present on a surface.

The lipids in a fingerprint are relatively durable and long-lasting when exposed to the environment. Lipids do not deteriorate as readily as salts through exposure to moisture and, unlike amino acids, lipids are always present in a fingerprint. Advantages to using lipids in the fingerprint as a basis for detection are well recognized and several methods have been developed as a result.

The method widely known as "dusting for prints" involves depositing a colored powder on a surface suspected of bearing latent prints. The powder adheres to lipid residue on a surface and the loose excess powder is delicately brushed off in a tedious and labor intensive process, thereby disclosing any latent fingerprints. The disclosed prints may then be physically "lifted" from the surface with adhesive tape and preserved on a piece of card stock.

In another method iodine crystals are warmed causing the sublimation of the crystals and the gas thus produced is blown or wafted over the surface being examined for latent prints. Iodine gas reacts with the lipids, causing the latent print to become visible. The fingerprint image produced by this method is evanescent and will fade, eventually vanishing over time. Photographic records of the freshly disclosed prints may be made, or chemical fixatives can be applied to halt the deterioration of the disclosed print. Iodine is a strong oxidizing agent and some forensic investigators may avoid its use as it causes rapid destructive rusting of metal.

Recent developmental work in the field of fingerprint detection has yielded new detection methods including various fluorogenic visualization and cyanoacrylate (C/A) fuming techniques.

In the fluorogenic visualization of amino acids, the latent image is treated with one or more chemical reagents which react with and covalently bond with compounds in the print to form a fluorescent chemical product. The image of the latent print is then viewed or photographed with the aid of an optical filter and under illumination of light of appropriate wavelength to cause excitation and fluorescence of the image. The enhanced detectability of latent images by application of fluorogenic rather than color-development techniques has stimulated research resulting in the development of a number of useful reagents for amino-acid fingerprint detection. Among these are ninhydryn, 5-methoxyninhydryn, 4-chloro-7-nitrobenzofurazan (NBD)-chloride, 1–8 diazafluorene-9-one (DFO), aminoninhydryns and 5-thioninhydryns.

Luminescent dyes are also used to enhance fingerprints developed for use in conjunction with C/A fuming techniques. Many dyes, such as Rhodamine 6G, Ardrox or Basic Yellow 40 are readily available and routinely used either to introduce contrast or to increase detection sensitivity in these techniques. Europium chelates have also been explored for this purpose.

Recently, a lipid-specific lanthanide-based method for latent fingerprint detection has been proposed. Although this method offers some promise for the detection of latent lipid images, its practical implementation is subject to a number of problems and drawbacks. One of the drawbacks is that the multi-step multi-reaction lanthanide chemistry used in the technique is complex. Lanthanide ions have very poor energy absorption and hence are not efficiently excited by energy sources. In order to enhance fluorescence the lanthanide ions are chelated with organic ligands which exhibit good energy absorption properties and are able to transfer their excitation energy to the lanthanide via resonant energy transfer. The application of this technique to the detection of latent lipid images is even further complicated in that it requires the lanthanide ion to be reacted with a conjugating ligand (non-luminescent) to provide some specificity toward lipids and further reaction with a sensitizing ligand to generate lanthanide luminescence through energy transfer.

Another drawback of the lanthanide-based method is that it is subject to high background fluorescence which reduces contrast and detection sensitivity of the process. The source of the high fluorescence background in the lanthanide-based method is two-fold. First, the method requires excitation via ultraviolet (UV) illumination and many surfaces on which fingerprints are located, for example, on biological surfaces (leaves, wood, etc.), plastic, paper, glass, and a host of other materials exhibit some degree of background fluorescence when excited by energy in the UV and short-wavelength visible spectrum range. Second, the sensitizing ligand required to generate lanthanide luminescence itself causes non-specific background fluorescence. The long luminescence lifetime of lanthanide chelates (hundreds of microseconds to milliseconds in duration) permits, in principle, the reduction of background luminescence through time-resolved detection techniques. The time-resolved techniques require pulsed illumination (e.g., a pulsed argon ion laser) with a delay-gated detection device. It will be well understood that these detection techniques introduce additional complexity and expense to forensic work.

The lanthanide-based method is even further restricted in its use according to the age of the print being detected. It appears that the lanthanide method is only suitable for use on prints which are quite fresh and works poorly, if at all, on older fingerprints.

The limitations and shortcomings of the various known techniques coupled with the great potential in using the lipid residues present in a latent fingerprint for forensic analysis have created a pressing need for development of better detection methods. Ideally, a detection method should be capable of generating a lipid-specific fluorescent image with low background fluorescence and a high contrast image. The technique should provide a high detection sensitivity, use a simple one-step chemical process, and create images amenable to recording with inexpensive, largely conventional cameras and optical equipment and simple, low-power illumination sources. Furthermore, it is advantageous for the method to generate and capture images in the presence of full ambient illumination on site whether the light is natural sunlight, incandescent, fluorescent, or from another light source.

SUMMARY OF THE INVENTION

An object of the present invention is to provide a method for the detection of latent lipid images such as those formed by fingerprints.

Another object of the invention is to provide a method for the detection of latent lipid images using a dye which fluoresces on exposure to an appropriate light source when the dye is in contact with a lipid, but in the absence of contact with a lipid the dye fluoresces little or not at all.

Yet another object of the invention is to provide a method for the detection of latent lipid images using a dye which does not require chemical reaction with, or covalent bonding with the lipid in order for detection of the lipid to occur.

A further object of the invention is to provide an apparatus for detection of latent lipid images.

Still another object of the invention is to provide a method of taking and recording distinctive patterns and markings of the skin, including fingerprints, footprints and handprints for identification purposes.

Other objects of the invention will be in part obvious and in part pointed out more in detail hereinafter.

These and other objects of the invention are achieved through the method of applying a dye to a surface having a latent pattern formed of lipid material. The dye is characterized as having an affinity for lipids and for fluorescing when in contact with a lipid and exposed to an appropriate energy source, thereby forming a fluorescing image of the latent lipid pattern. Viewing of the fluorescing image may be accomplished using an optical filter appropriate for detecting the wavelength of the fluoresced light. The revealed image may also be observed, recorded and preserved by any conventional film or digital camera or other imaging means with the use of film, filters or conventional optical equipment appropriate for recording the particular wavelength light which is fluoresced by the image.

The dyes having utility in the invention are dyes which exhibit sensitivity to the environment in which they are present, that is, the dyes are capable of fluorescence when in contact with lipids, but possess little or no ability to fluoresce when in a non-lipid environment such as water or polar solvents. The dyes having particular utility in the invention are dyes in the styryl family of dyes.

The invention accordingly comprises the several steps and the relation of one or more steps to the others, and the apparatus possessing the features, properties, and relation of elements as set forth in the following disclosure.

DETAILED DESCRIPTION OF THE INVENTION

Figure 1:
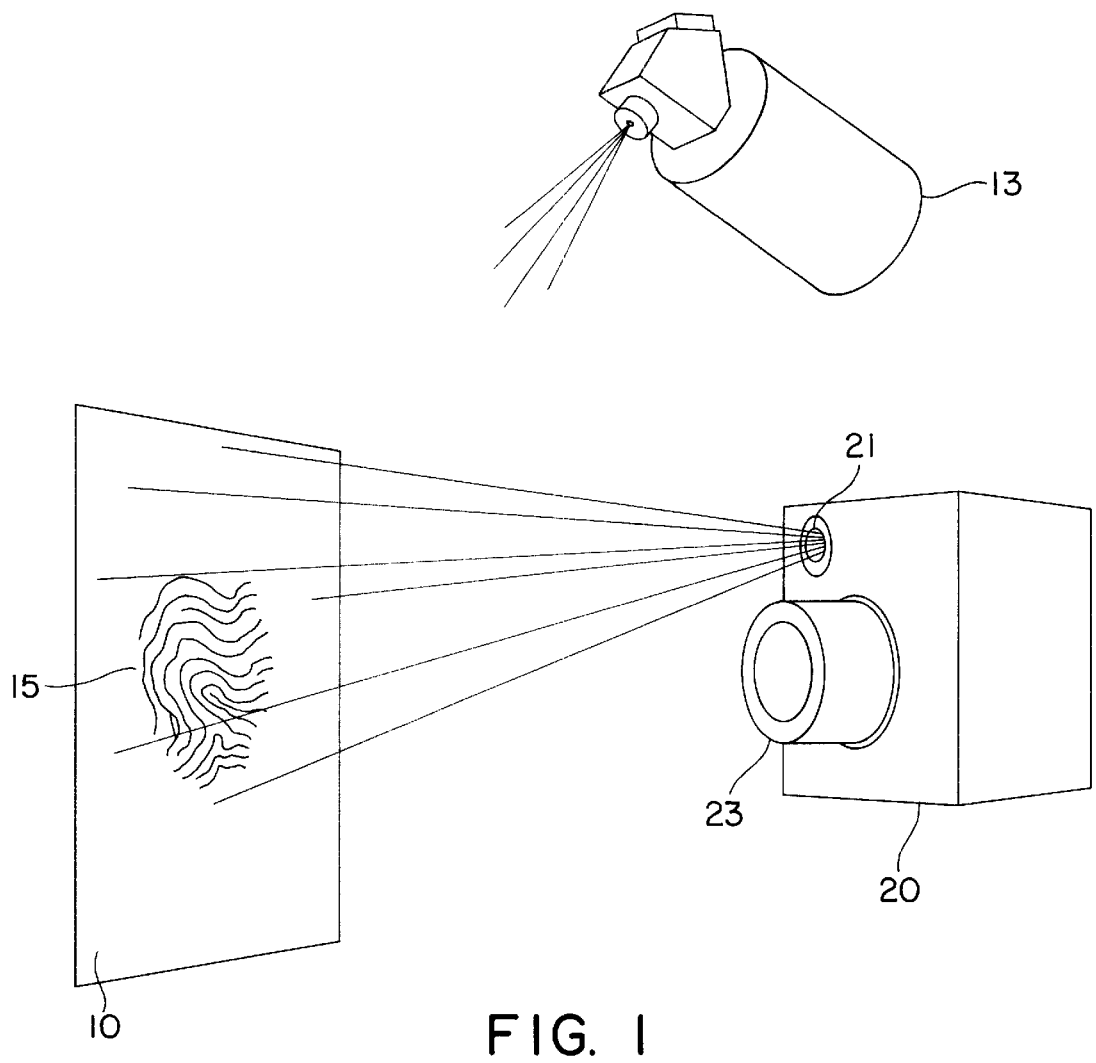
FIG. 1 is a schematic representation of a method of detecting a latent fingerprint image according to the invention.

FIG. 1 illustrates in a schematic form one embodiment of the method of the invention. A surface 10 suspected of having latent fingerprints is sprayed by a spray bottle 13 with a solution containing a fluorescing dye. It will be appreciated that other ways of applying the dye solution to a surface may be used including, but not limited to, dipping an object in the dye solution, or flowing the dye solution over the object, such as with a wash bottle or pump-like instrument. As the solution comes in contact with the surface being tested, it is believed that the lipophilic ends of the dye molecules in proximity of lipids on the surface orient themselves or otherwise associate with the lipid enabling their fluorescence to be detected when excited.

A compact portable detection and recording device 20 is optically aligned with the dye treated surface. A light source 21, such as an LED, emits light energy of an appropriate wavelength to illuminate the dye-treated surface. Dye on the surface which has come in contact with the lipids of a latent fingerprint 15 fluoresces due to excitement from the light source. The fluoresced light detected by the lens assembly 23 forms a fingerprint image that can be observed by the operator of the device and/or recorded by film, electronic or other means.

The method of the invention thus comprises the steps of treating a surface to be analyzed for the presence of latent lipid images by applying a fluorescing dye to the surface, exposing the treated surface to an appropriate source of energy to cause the dye to fluoresce; and detecting the presence of latent lipid images on the treated surface by optical or other means. Optionally, the method may further include recording the image and surrounding environment by photographic, electronic or other imaging means.

The dyes employed in this method are generally those dyes which are amphipathic or lipophilic and which fluoresce on exposure to an appropriate light source. More specifically, the preferred dyes are those dyes which exhibit the following properties:

The dyes are amphipathic or lipophilic and are suitably attracted to the type and the quantity of lipids typically present in a latent fingerprint;

The dyes fluoresce when in contact with a lipid (i.e., when in a lipid environment) and are exposed to an appropriate source of illumination or energy to cause the dyes to fluoresce;

The dyes do not fluoresce, or fluoresce only a minimal amount when in the absence of contact with a lipid (i.e., when in an aqueous or polar environment) and are exposed to appropriate illumination or energy which would otherwise cause the dyes to fluoresce;

The dyes possess strong absorption bands in the blue-green spectral range (about 450 nm) or at longer wavelengths, to reducing background fluorescence;

The dyes can be excited by light provided by inexpensive light-emitting diode (LED) light sources;

Some of the dyes fluoresce in the far red or near infrared (NIR) spectral range where emissions from background fluorescence are low to provide high contrast and sensitivity;

The dyes have large Stokes shifts (approximately 150 nm) which permit the rejection of scattered excitation light with inexpensive optical filters;

The dyes are highly environmentally sensitive in that they are virtually non-fluorescent in an aqueous environment, but fluoresce strongly in a lipid environment;

The dyes are suitable for use via direct application to a latent fingerprint, wherein the dye is applied directly to the latent fingerprint and the disclosed image can be observed and recorded under appropriate light without the need for subsequent treatment or reaction with other chemicals;

The dyes may be used in the form of aqueous solutions;

The dyes do not require covalent bonding with the lipid in order to detect the fingerprint image; and The dyes are water soluble and can be readily used and applied in the field in the form of an aqueous solution.

The family of styryl dyes meets these requirements and provides even further advantages in the method of the present invention. Dyes of the styryl family may typically be obtained through aldol condensation or by palladium-catalyzed coupling procedures. A number of such styryl dyes are available commercially from Molecular Probes, Inc. (Eugene, Oreg.).

The formulas which follow are a representative, but not exhaustive list of examples of the styrl dye materials intended for use in this invention:

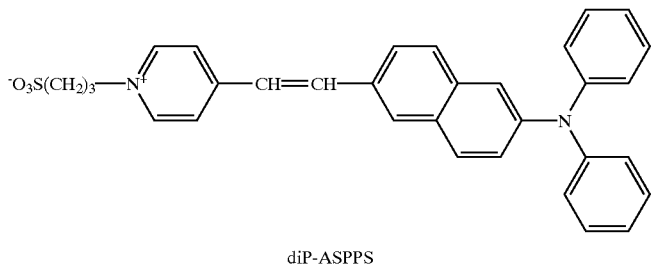

diP-ASPPS

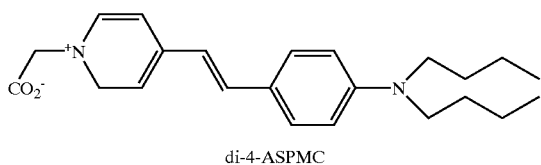

di-4-ASPMC

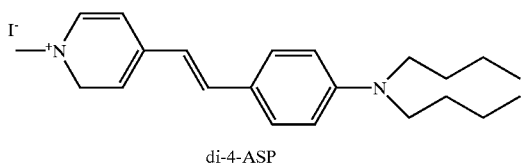

di-4-ASP

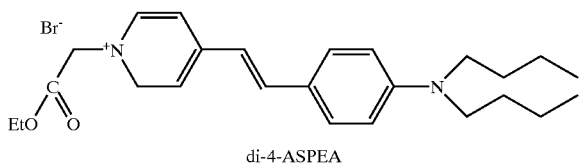

di-4-ASPEA

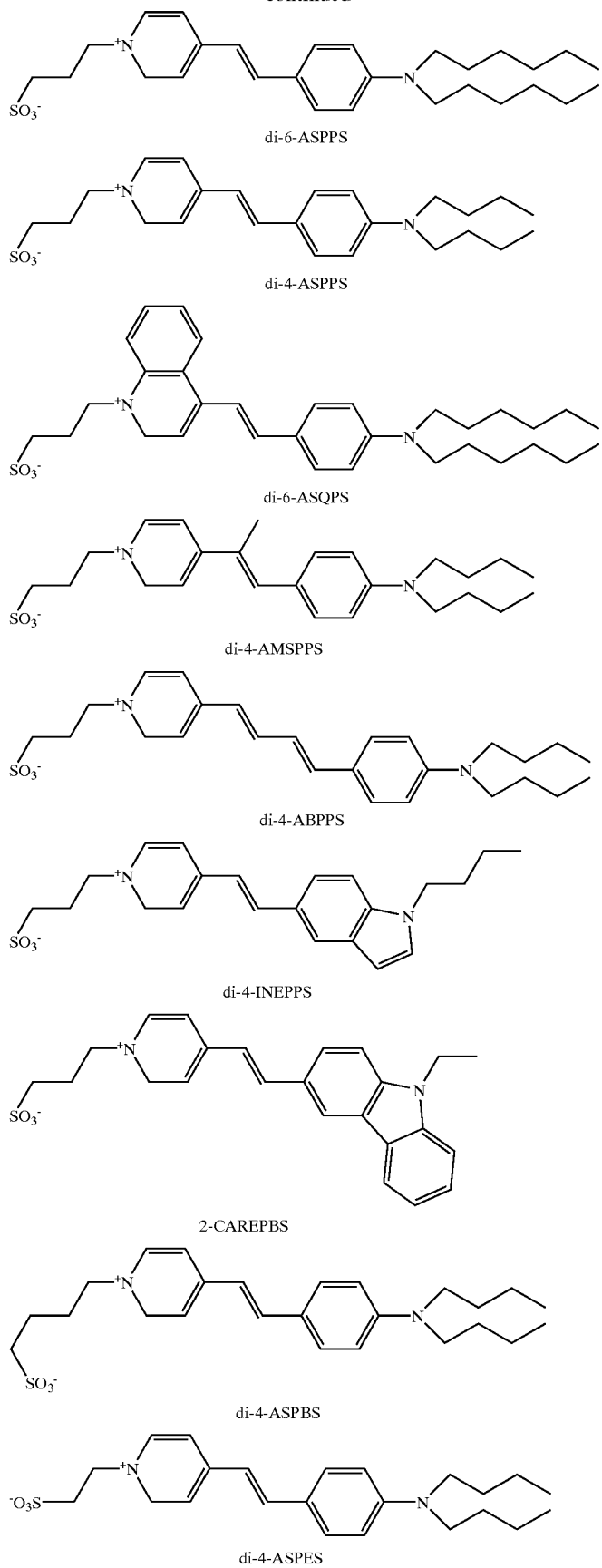

-continued

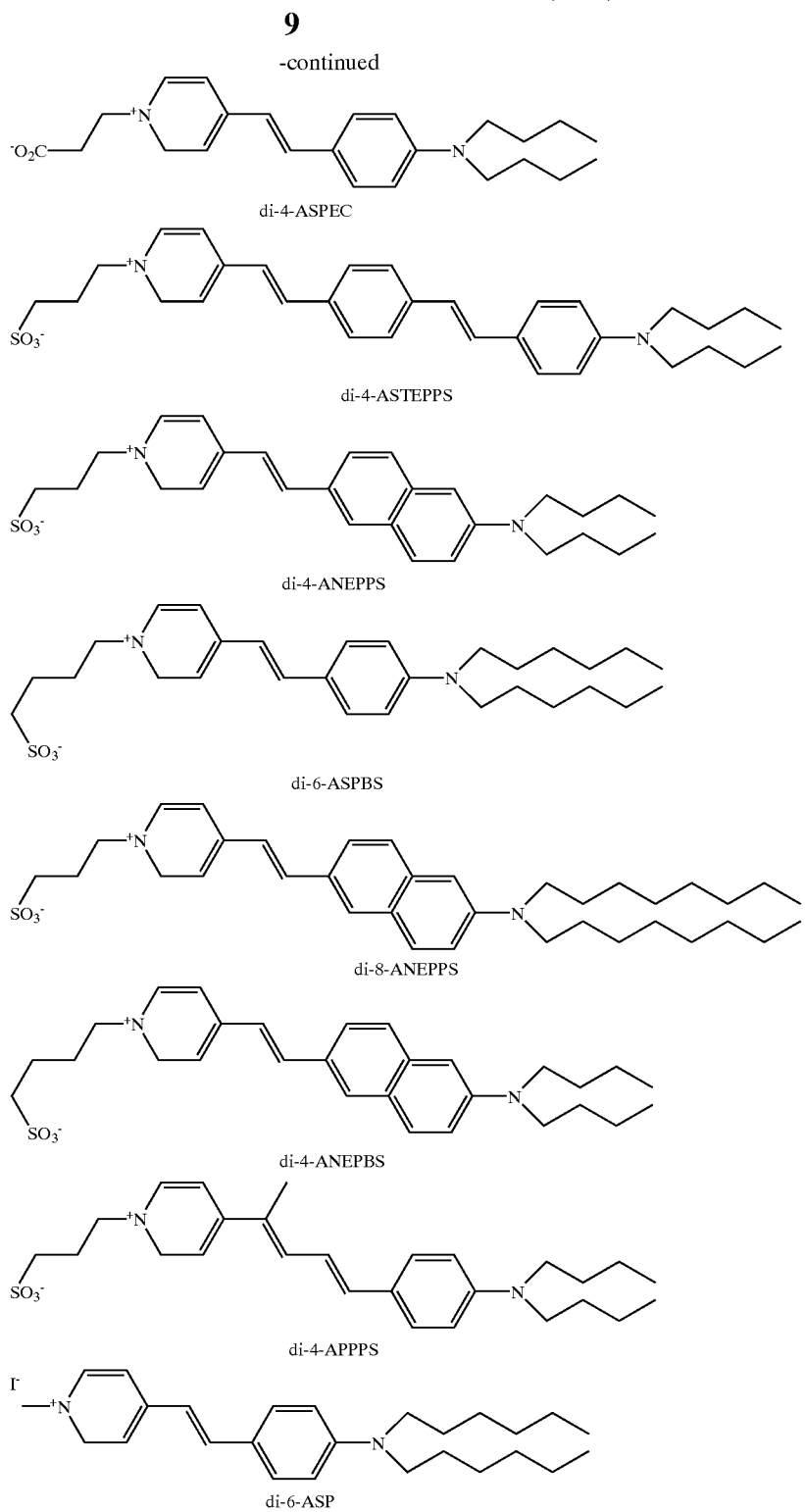

The most preferred styryl dyes employed in connection with the invention are amphipathic in nature, that is, their molecular structure possesses both a lipophilic end and a hydrophilic end. In the presence of lipids, such as the lipid residue of a latent fingerprint, the lipophilic ends of the dye molecules associate themselves in micelle fashion with the lipid. It is believed that the concentration and orientation of the molecules in the presence of a lipid account for the strongly fluorescent behavior of the dye. In an aqueous or other polar environment, a similar concentration and orientation of the dye molecules does not occur and consequently, the dye exhibits no or very low fluorescence.

The dyes of the invention are typically applied in the form of a solution. The solutions are obtained typically by first preparing a stock solution by dissolving a small amount of dye in a suitable solvent. For example, the dyes of the present invention were obtained as 5 mg samples. To prepare a stock solution the 5 mg sample was dissolved in 5 ml of a solvent, such as DMSO (dimethyl sulfoxide). The stock solutions thus obtained were found to be relatively stable, having a shelf life on the order of several months. It will be appreciated that the concentration of the stock solutions thus prepared were approximately 1 millimolar solutions, depending on the molecular weight of the particular dye used. For example, a stock solution prepared from a 5 mg sample of di-8-ANEPPS had a concentration of $1.687 \times 10^{-3}$ moles/liter. It will be appreciated that the molar concentration will vary from dye to dye according to this method of preparation, as the molecular weight will vary between dyes. Once the stock solution was prepared, working solutions of the material could be prepared through dilution to obtain solutions of the desired concentration. The dye of the invention can be present in the solution over a wide range of concentrations. However, for ease of application and convenience the dye is used in molar concentrations varying from 1 $\mu$M to 10 $\mu$M, with dye concentrations preferably within the range of 3 $\mu$M–7 $\mu$M.

Suitable diluents and solvents for the dyes of the invention are polar solvents, such as distilled water, dimethyl sulfoxide TRIS-acetate, and aqueous saline solution. It was found that the working solutions of the dyes prepared from the stock solutions were not pH sensitive and that distilled water was a suitable diluent for preparing a working solution from the stock solution. TRIS-acetate can be used in the form of a buffered solution at a pH of about 8.3 and the saline solution can be used in the form of a phosphate buffered saline solution with a pH of about 7.2. Other diluents may be used which do not hinder the operation of the invention.

Certain members of the styryl family may exhibit long wavelength (far red and near infra-red) excitation and emission which result in a dramatic reduction in non-specific background fluorescence as compared to dyes which exhibit excitation from UV or visible light. Also, the use of these preferred dyes results in a significant reduction in Rayleigh and Raman scattering which have a $1/\lambda^4$ dependence which translates into low background fluorescence and increased contrast and higher detection sensitivity.

An apparatus for detection and recording of latent lipid images includes an energy emitting source for projecting energy at a surface to which a fluorescing dye has been applied. Energy of the proper intensity and wavelength will cause the dye to fluoresce. The apparatus further includes a means for observing, detecting, processing and recording the fluorescing image and any image created by ambient light.

Figure 2:
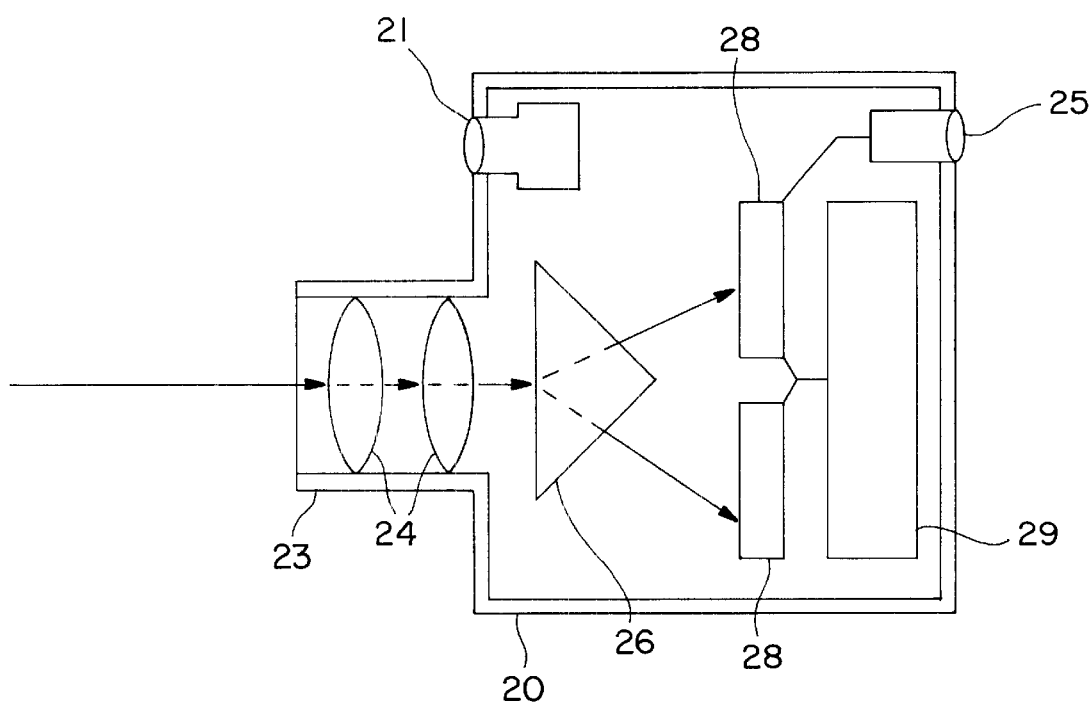
FIG. 2 is a schematic representation of an embodiment of a latent fingerprint image detection and recording apparatus according to the invention.

With reference to FIG. 2, a schematic block diagram of one embodiment of the detection and recording device 20 of the invention is shown. This particular device utilizes a digital apparatus for detection and recording of latent fluorescing images, although other optical and film recording devices are comprehended by this invention.

The detection and recording device 20 has an illumination source 21 for projecting light energy at a treated surface. The illumination source can be any device which produces energy, particularly light energy of the wavelength and intensity necessary to cause excitation and fluorescence of the dye used. Common illumination sources for use in this invention include diode lasers and light emitting diodes (LEDs). LEDs and diode lasers are relatively inexpensive compared to argon lasers. Moreover, LEDs and diode lasers are known to be durable, small, light, rugged (laser gun sights are able to withstand 1000 g impacts), and efficient (mW vs. kW power requirements for an argon laser). Because of this high efficiency, diode lasers are easily battery-powered, thus making the hand-portable detection system a low-cost, practical forensic tool.

Ambient light and fluorescent light produced by the excited dye enter the lens assembly 23 and are focused by the lens elements 24. Aiming of the device and detection of a latent image is aided by the view finder 25. In a digital camera device a miniaturized viewing screen such as made from a liquid crystal diode may be used as a viewfinder.

In this embodiment the fluorescence and ambient light which enter the lens are then passed to a light splitting device 26 such as a dichroic light splitter. The splitter separates the light image into a fluorescence wavelength image and a visible wavelength image and each image is selectively directed to digital image sensor 28 such as a silicon-based charge coupled device (CCD). The image sensor digitizes the analog image and then transfers the image on command to storage in a recording means 29 or memory. Preferably, images of both the fluorescence image and visible light image are recorded for the purpose of orienting the fingerprint image in its surroundings.

Silicon-based charge-coupled device (CCD) detectors have excellent detection efficiency in the red and NIR region of the spectrum. This means that recording high-resolution images can be efficiently made employing relatively inexpensive, off-the shelf digital CCD-based cameras. Consequently, the invention provides all the advantages of digital data, such as rapid transmission over telephone lines and sophisticated image processing.

It will be appreciated by those of skill in the art that an analog embodiment of the detection and recording device is fully within the scope of this invention. Such a device would include an illumination source and a camera with film and/or light filters appropriate for visually observing the image and recording the image on film.

Another means for viewing and detecting fluorescing images is a simple optical direct viewing device such as a loupe with a filter which passes the wavelength of the fluorescent light, allowing the viewer to see the images.

The method of the present invention was used in a number of examples to image and document latent fingerprints. A cooled CCD camera, model KX1 commercially available from Apogee Instruments (Tucson, Ariz.) was used in the examples. The camera uses an Eastman Kodak (Rochester, N.Y.) Grade 2 KAF-0400 CCD sensor with an array size of 768×512 with a pixel size of 9 $\mu$, thus yielding 393,216 pixels with a 14 bit resolution. The active area of the sensor was 6.9×4.6 mm, the pixel depth was 85,000 electrons with a system gain of 5 electrons per ADU. The maximum quantum efficiency of the array was determined to be 40%. Integration time was shutter controlled with exposure times of 0.02 seconds to 2.89 hours in 0.01 second increments. The camera was thermoelectrically cooled with forced air driven by a fan for heat exchange with the ambient environment. The cooling unit was able to maintain the temperature of the camera about 37° C. below ambient temperature. The temperature stability of the camera was determined to be +/−0.1° C. An f1.4 camera lens was used to image the fingerprints in the tests.

The camera was connected to an ISA-bus digital controller card and operated via CCDSOFT image acquisition and processing software, commercially available from Software Bisque (Golden, Colo.). The camera was mounted approximately 70 cm above a stage on which the test examples were photographed. Spatial resolution of the camera was determined to be between 31 and 36 line pairs per mm using a USAF 1951 resolution test chart. Based on the test chart results the spatial resolution of the camera was considered to be marginal, but adequate for the purposes of the examples which followed.

A light source was developed for illuminating the surface to which the fluorescent dye solution was applied. In designing the light source it was determined highly desirable for the light source to be low cost, portable, power efficient and that the operation of the light source be similar to conventional photographic lighting sources. Although high-pressure xenon arc lamps, mercury lamps or lasers can be used to illuminate the surface being investigated, such light sources are presently too cumbersome and their power demands too high to meet the requirements of portability and rapid, on-site imaging and documentation of fingerprints. In contrast, LED light sources are extremely compact, efficient and rugged, have low power consumption demands, but a high spectral radiance, that is, they provide a high output of light energy within a narrow spectral band. Commercially available LEDs can be obtained with an output of about 5 mW in emission bands very well matched to the absorption bands of dyes useful in the present invention.

The light source used in the following tests consisted of a cluster of five blue (450 nm wavelength) 15° LEDs commercially available from Nichia America Corp. (Mountville, Pa.) under the designation NSP 500S blue. The cluster of LEDs was mounted behind a 2"20° holographic diffuser and was used both with and without a 455DF22 bandpass filter commercially available from Omega Optical Co. (Brattleboro, Vt.).

Other light sources were used for comparison with the LED light source described above. One alternative light source was a 75 watt tungsten-halogen lamp optically connected to a 2' long fiber optic light guide leading to an Omega Optical Co. 455DF22 bandpass filter and two 20° holographic diffusers to produce a uniform field of illumination. Another light source was an argon laser.

Post processing of the digital images was accomplished with CCDSOFT from Software Bisque and CANVAS-6 from Deneba Systems Inc. (South Miami, Fla.) to provide improvement and enhancement of the recorded images. The software provided such photoimaging enhancements as contrast manipulation, smoothing, and edge enhancement. Practitioners in the art will recognize other software programs specifically designed for fingerprint image enhancement have further features including ridge thinning to improve the clarity of the digital image of the fingerprint.

A variety of substrates were used in the examples to evaluate the ability of the prototype dyes and camera equipment to image and document latent fingerprints and similar images on various materials. The substrates used include rough textured white paper (business card stock), photocopier paper, white file card stock, newspaper, manila envelopes, brown paper bags, white, grey and brown cardboard box stock, paper money, glass, black electrician's tape, aluminum foil, glossy white finished paper, yellow POST-IT notepad paper available from 3-M Corp. (Minneapolis, Minn.), white, black, brown, green and red construction paper, water color paper of various surface textures, and fresh pig skin. Samples of each material were cut into 1"×3" test substrate rectangles.

Latent fingerprints were applied to each of the substrate samples using a reproducible technique. The investigator rubbed a finger on the surface of his nose or forehead to acquire an amount of naturally occurring sebaceous secretions on the surface of the finger. The investigator then lightly and evenly contacted the finger with the surface of the substrate sample to form a latent fingerprint thereon. In addition, a limited number of other examples were prepared in which fingerprints were formed using model lipids such as butter, lard and olive oil. A few other examples were prepared in which a non-fingerprint latent image was formed using a rubber stamp bearing the inventor's name and samples of the model lipids.

After the latent fingerprints and other images were applied to the substrate, sample solutions of dye were prepared for application to the substrates. A first solution 5 mg of di-8-ANEPPS dye was dissolved in 5 ml of dimethyl sulfoxide to make a stock dye solution.

Approximately 200 $\mu$l of the stock dye solution was mixed with 50 ml of various diluents including distilled water; TRIS-acetate buffer at a pH of 8.3; and a phosphate buffered saline solution at a pH of 7.2 to make working solutions wherein the dye is present in polar concentrations ranging from 0.34 $\mu$M to 6.75 $\mu$M. It was found that suitable results were obtained using dye solutions wherein the dye is present in molar concentrations in the range of 3 $\mu$M to 7 $\mu$M. A dye solution with a molar dye concentration of $6.75 \times 10^{-6}$ was used extensively in the examples. Latent fingerprints stained with dye in concentrations below 3 micromoles per liter stained lightly and required longer integration to generate a good image. At concentrations above 7 $\mu$M fingerprints stained so intensely that ridge detail was often obscured.

The dye was applied to the substrate using two different application methods. In a first method, referred to as the "dipping method", the substrate bearing the latent fingerprint was placed in a beaker containing the dye solution with the fingerprinted area of the substrate brought in full contact with the dye solution. The fingerprinted area of the substrate was left in contact with the dye solution for periods of time ranging from 10 seconds to several hours. It was found that the most useful dipping times for obtaining good fingerprint imaging were in the range of 60–120 seconds. At staining times less than 60 seconds the fingerprint stains too lightly to yield an optimal image. At times much in excess of 120 seconds, the finger paint ridge detail can be obscured and possibly, some lipid is washed away. In any event, the image quality may be reduced at excessive staining times. In the second method of applying the dye solution to the fingerprinted area of the substrate the solution was sprayed using a pump spray bottle (atomizer). When spraying, care should be taken to apply an even coating of the dye solution to obtain the best results. The area should be dried for optimum viewing of the image. When the substrate is wet or even damp the stained print does not fluoresce brightly. As the substrate dries the fluorescence intensity increases.

After application of the dye solution, the substrates were permitted to dry. Drying can be carried out under ambient conditions, or can be speeded through exposure to moving air. Based on limited data, poor image quality may result when heat is used to accelerate drying of the stained print. Thus, it is envisioned a hand-held fan with selectable speed settings may be used to assist in speeding the drying time.

While both the dipping and spraying methods were shown to be effective, dipping provided more uniform results. Spraying, which would appear to be a very practical field method of applying the dye required the use of greater care to avoid spotting or streaking due to uneven application of the dye solution. It is further envisioned that the problems of streaking and spotting can be reduced through the use of finer and more uniform atomizing mists from the sprayer and further training and practice of the technician applying the dye solution.

Subsequent to drying, the substrates were placed within the field of view of the CCD camera described above. The substrates were placed in a sample holder and pressed flat under a glass cover to insure a uniform field of focus for the camera. Samples were illuminated using various light sources (blue LED, 75W tungsten-halogen lamp or argon laser) as described above.

EXAMPLE SERIES 1

In a first series of examples, substrates business card stock which had been imprinted by means of a rubber stamp lightly coated with one of the model lipids (butter, lard or olive oil) and subsequently treated with a $6.75 \times 10^{-6}$ molar aqueous solution of the dye di-8-ANEPPS in distilled water were digitally photographed using a 15 second exposure and a bandpass emission filter with a transmittance peak at 550 nm wavelength with a full width at half maximum of 10 nm. No post-processing was used to enhance the photographs obtained. The print of the inventor's name made by the rubber stamp fluoresced brightly in the digital photographs and was very clear and legible. Only a faint amount of background fluorescence was observed emanating from either the substrate or the dye which was not in contact or proximity to the lipids in the print. However, the unprocessed photographs showed a very strong contrast between the fluorescing areas and the essentially non-fluorescing background. Further contrast may be obtained, if necessary, through suitable image processing software.

EXAMPLE SERIES 2

The sensitivity of the method of the invention was demonstrated by applying a spot of about a 10 $\mu$l aliquot of a solution of lard diluted in chloroform. The lard solutions were graduated in concentration so that the amount of lard contained in and deposited on the substrate by a 10 $\mu$l aliquot of the solution ranged from 50 $\mu$g to 5 ng of lard. After treating the substrates with the di-8-ANEPPS $6.75 \times 10^{-6}$ molar solution in distilled water by dipping for 80 seconds, the substrates were dried and then illuminated with a tungsten-halogen lamp and photographed with the CCD camera. The images produced by the lipid spots were analyzed by comparing the average signal intensity produced by the spot image to the average intensity of the background (the non-spotted part of the substrate) to arrive at a contrast ratio. No significant differences were noted in the contrast ratios over the range of lipid concentrations tested. It will be appreciated by those skilled in the art that a 5 ng/10 $\mu$l lipid concentration does not represent a minimum detection limit of this invention. It will be further appreciated by those skilled in the art that the concentration of lipid residue found in a fingerprint is typically about 1 ng/10 $\mu$l which is several times greater than the lower limit of lipid used in this example. Therefore, the present invention provides an exquisitely sensitive method and apparatus for detecting latent fingerprints.

EXAMPLE SERIES 3

In a further series of examples, latent fingerprint images made on substrates with natural sebaceous secretions as described above were examined. The substrates bearing the latent sebaceous fingerprints were treated with one of solutions of the dyes: di-8-ANEPPS; di-4-ANEPPS; and di-phenyl ASPPS. When the substrates were dried the latent image remained invisible to the human eye when illuminated with ambient light. However, when illuminated under a blue light source (all of the blue sources used worked well) a well-stained fingerprint was revealed as a faint red colored blur. When viewed through a bandpass or long-pass filter to block the scattered blue light, a very clear, bright yellow fingerprint could be clearly seen. In the images, the ridges of the fingerprint appeared as brightly fluorescing lines. The valleys between the fingerprint ridges remained dark and of low or no fluorescence. It was noted that all three dyes exhibited emission maxima near 590 $\mu$m wavelength and the dye di-phenyl ASPPS exhibited the strongest fluorescence.

EXAMPLE SERIES 4

Forensic scientists have been faced with the daunting problem of imaging and documenting latent fingerprints on human skin. Background fluorescence for skin, both animal and human, is high. In fact, at 450 nm wavelength background fluorescence is typically several times higher than the background fluorescence emissions from white paper such as the back of a business card. Latent fingerprints formed from naturally occurring sebaceous secretions were made on samples of fresh pigskin obtained from a grocery store. In this example the pigskin serves as a particularly close model for human skin. The pigskin samples were treated with solutions of the fluorescent dyes of the invention and in each instance the diluent from the dye solution was permitted to dry. An argon laser was used to illuminate the latent fingerprint and a photograph was made with the CCD camera. A visible and readable fingerprint image was produced by each dye. However, the best results were obtained using the di-phenyl ASPPS dye.

EXAMPLE SERIES 5

The use of the invention in the imaging and documentation of aged latent prints was demonstrated. Fingerprints formed with naturally occurring sebaceous secretions were formed on white paper substrates. The fingerprints were aged, then treated with a 6.75 $\mu$M solution of di-8-ANEPPS dye for 120 seconds. The substrates were dried and then photographed with the CCD camera under illumination of a tungsten lamp and using a +455, DF22 band pass filter, and a +2 diffuser. Good fingerprint images were obtained in the test up until the prints were aged about three weeks. However, after three weeks ridge detail diminished considerably, apparently due to diffusion and spreading of the lipids in and on the substrate. Eventually the fingerprint images became so diffuse that ridge detail was lost when the CCD camera obtained photographs were observed without enhancement or image processing. However, it is envisioned that ridge detail could be recovered using image processing software at this stage and after the fingerprints are aged more than three weeks.

It was found that once a latent fingerprint was treated with a dye of the invention the substrate could be dried and stored for a period of months in a dark drawer at room temperature without significant deterioration of the image. The dyes were found to resist photobleaching, as no observable fading was noted after prolonged exposure to the excitation of blue-green illumination.

The utility of the present invention in conjunction with gathering forensic evidence from a crime scene is readily apparent. However, the invention has broader applications in the taking and recording of fingerprints, footprints, handprints and other distinctive skin patterns directly from an individual. For example, by forming on a surface a lipid image of a newborn infant's footprint, treating the lipid image with the fluorescing dye of the invention and recording the distinctive fluorescing image, identifying marks of an infant can be cleanly and easily recorded. The present invention thus can be used to avoid the traditional black inking of skin surfaces for the purpose of establishing and recording identity.

As will be apparent to those skilled in the art, various modifications and adaptations of the method and apparatus described above will become readily apparent without departure from the spirit and scope of the invention.

What claimed is:

1. A method of imaging a latent pattern of lipid residues comprising the steps of:

contacting the residues with a dye having an affinity for lipids, wherein said dye fluoresces when in proximity to the lipids and excited by an appropriate energy source;

exposing said dye to an energy source for exciting said dye to fluoresce; and observing the fluorescing image formed thereby; wherein said dye is one or more members of the dyes of the styryl family consisting of:

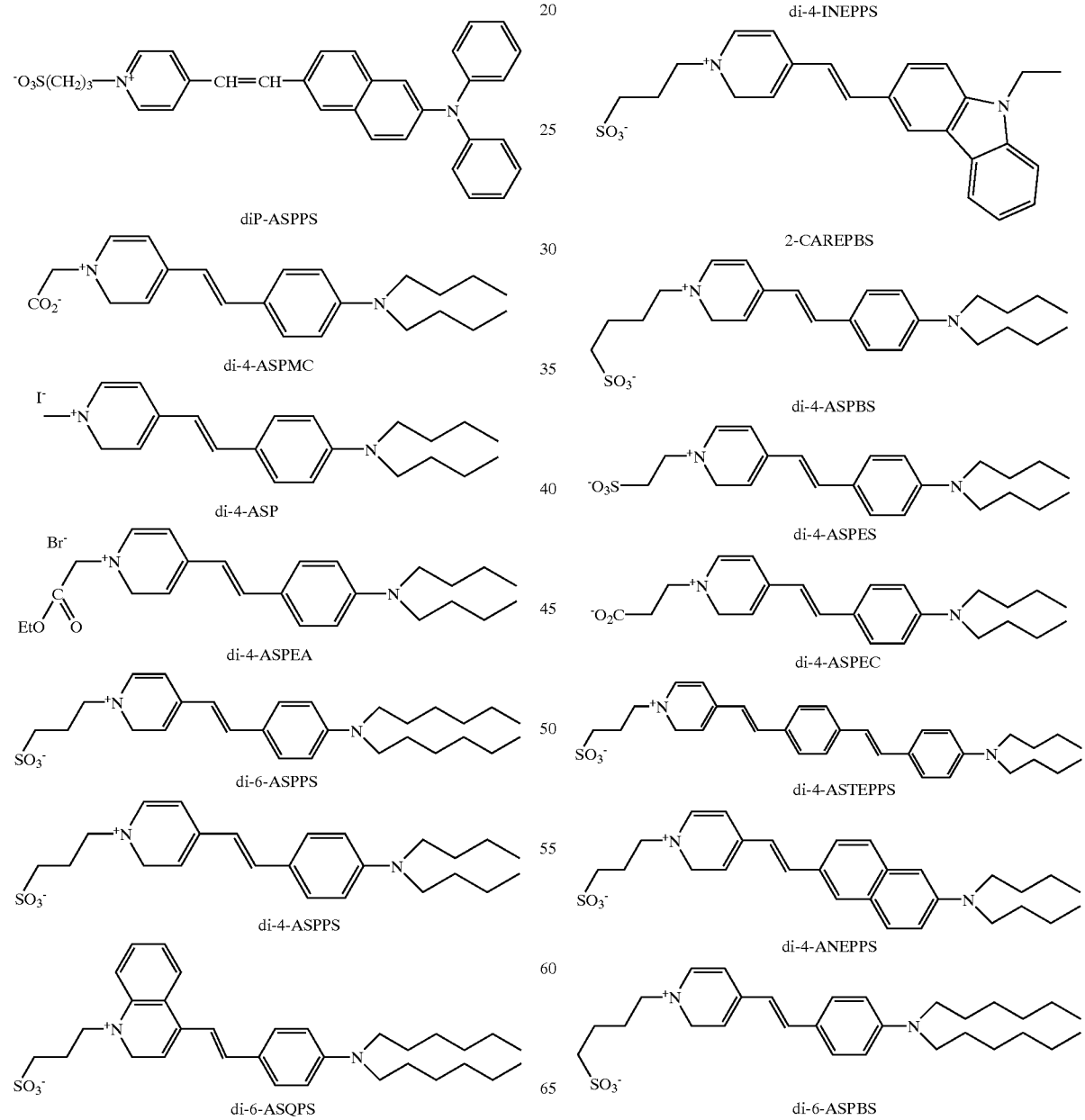

-continued

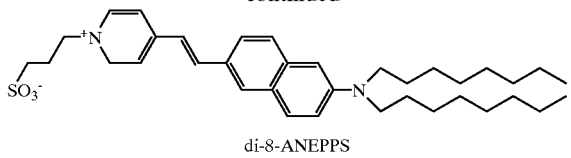
di-8-ANEPPS

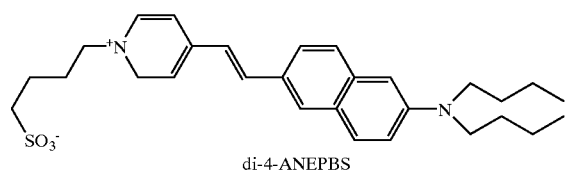
di-4-ANEPBS

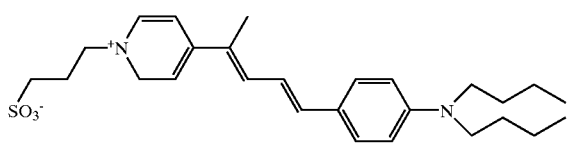
di-4-APPPS

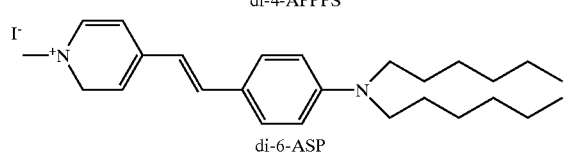
di-6-ASP

2. The method as claimed in claim 1, wherein said method further includes the step of recording the fluorescing image.

3. The method as claimed in claim 2, wherein a digital camera is used for recording the fluorescing image.

4. The method as claimed in claim 2, wherein an analog camera is used for recording the fluorescing image.

5. The method as claimed in claim 1, wherein said appropriate energy source is a light source within an emission spectrum in the blue-green range.

6. A method of imaging a latent fingerprint comprising the steps of:

contacting the latent fingerprint with a dye having an affinity for lipid residues which comprise the fingerprint, which dye fluoresces when in proximity of the lipid residues and excited by an appropriate energy source;

exposing the dye to an energy source to cause fluorescing excitation; and observing the fluorescing fingerprint image formed thereby; wherein said dye is one or more members of the dyes of the styryl family consisting of:

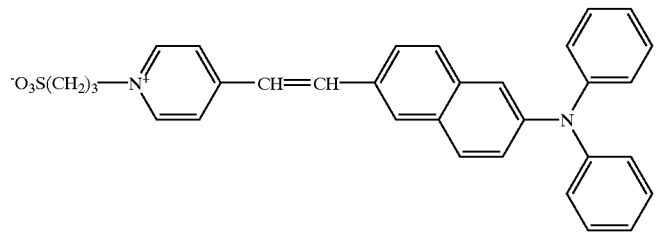
diP-ASPPS

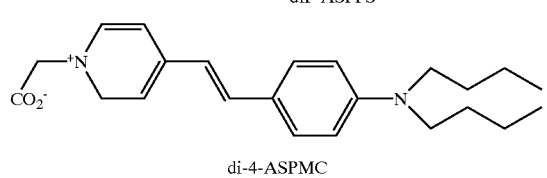
di-4-ASPMC

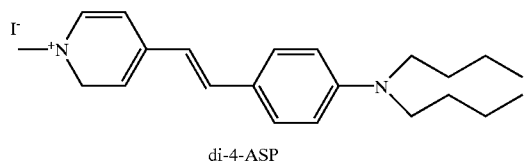
di-4-ASP

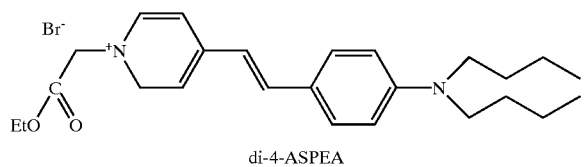
di-4-ASPEA

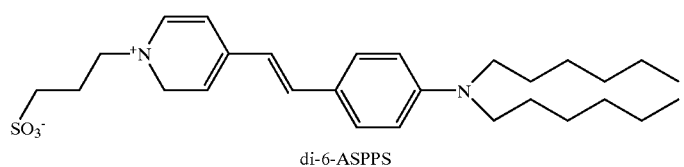
di-6-ASPPS

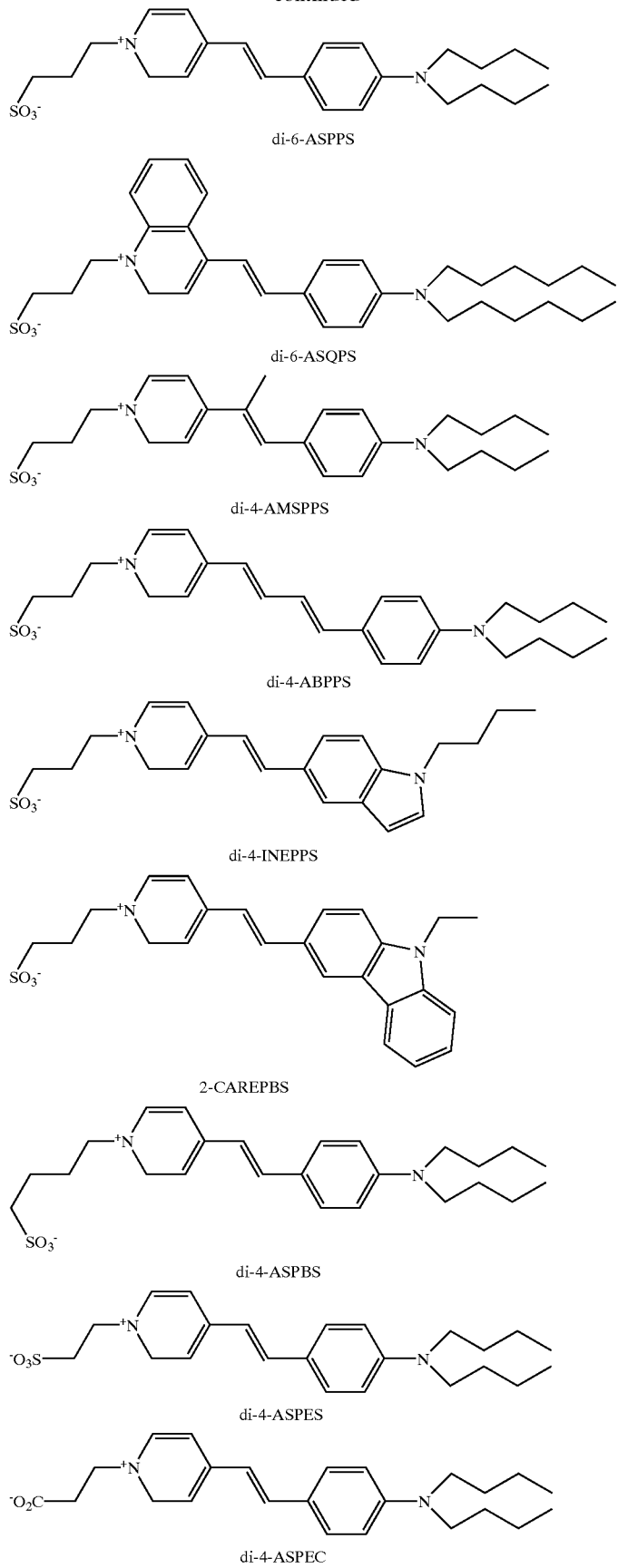

-continued

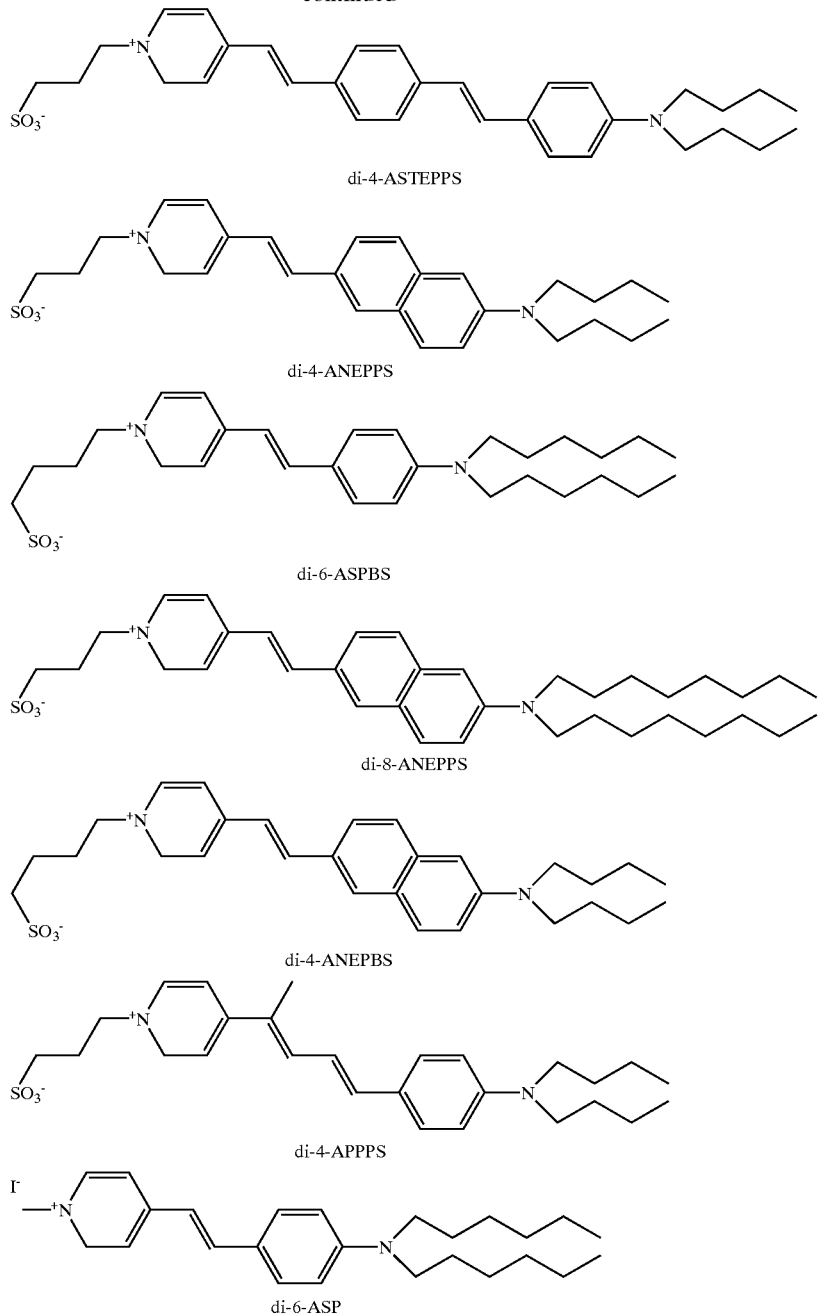

7. The method as claimed in claim 6, wherein said method further includes the step of recording the fluorescing image.

8. The method as claimed in claim 7, wherein a digital camera is used for recording the fluorescing image.

9. The method as claimed in claim 6, wherein an analog camera is used for recording the fluorescing image.

10. The method as claimed in claim 6, wherein said appropriate energy source is a light source within an emission spectrum in the blue-green range.

11. The method as claimed in claim 6, wherein said dye is in solution with a polar solvent, said solution having a dye concentration in the range of $0.5 \times 0^{-6}$ to $15 \times 10^{-6}$ moles of dye per liter solution.

12. The method as claimed in claim 11, wherein said polar solvent comprises one or more members selected from the group consisting of water, dimethyl sulfoxide, TRIS-acetate, and saline solution wherein the saline solution is in a concentration of about 0.6–1%.

* * * * *